(12) United States Patent
Kitamura et al.

(10) Patent No.: US 8,822,696 B2
(45) Date of Patent: Sep. 2, 2014

(54) LIGAND FOR ASYMMETRIC SYNTHESIS CATALYST, AND PROCESS FOR PRODUCTION OF ALPHA-ALKENYL CYCLIC COMPOUND USING THE SAME

(75) Inventors: Masato Kitamura, Nagoya (JP); Shinji Tanaka, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 87 days.

(21) Appl. No.: 13/499,404

(22) PCT Filed: Oct. 1, 2010

(86) PCT No.: PCT/JP2010/067279
§ 371 (c)(1),
(2), (4) Date: May 15, 2012

(87) PCT Pub. No.: WO2011/043272
PCT Pub. Date: Apr. 14, 2011

(65) Prior Publication Data
US 2012/0220780 A1 Aug. 30, 2012

(30) Foreign Application Priority Data
Oct. 7, 2009 (JP) ................................. 2009-233813

(51) Int. Cl.
*C07D 213/79* (2006.01)
(52) U.S. Cl.
USPC ........................................................ 546/326
(58) Field of Classification Search
USPC ........................................................ 546/326
See application file for complete search history.

(56) References Cited

PUBLICATIONS

Tanaka, S., et al., "Asymmetric Dehydrative Cyclization of w-Hydroxy Allyl Alcohols Catalyzed by Ruthenium Complexes," Angew. Chem. Int. Ed., vol. 48, pp. 8948-8951, (2009).
Seki, T., et al., "w-Hydroxy Allyl Alcohol-Rui no Shokubaiteki Fuseikanka," 40th Annual Meeting of Union of Chemistry-Related Societies in Chubu Area, Japan Yokoshu, vol. 40th, Total 4 pages, (Nov. 7, 2009).
Boivin, T.L.B., "Synthetic Routes to Tetrahydrofuran, Tetrahydropyran, and Spiroketal Units of Polyether Antibiotics and a Survey of Spiroketals of Other Natural Products," Tetrahedron Report No. 222, Tetrahedron, vol. 43, No. 15, pp. 3309-3362, (1987).
Hosokawa, T., et al., "Palladium(II)-Catalyzed Asymmetric Oxidative Cyclization of 2-Allylphenols in the Presence of Copper(II) Acetate and Molecular Oxygen. Study of the Catalysis of the Wacker-Type Oxidation," Journal of the American Chemical Society, vol. 103, pp. 2318-2323, (1981).
Massacret, M., et al., "One-Pot Preparation of Chiral 2-Vinyl-1,4-benzodioxane," Tetrohedron Letters, vol. 35, No. 33, pp. 6093-6096, (1994).

Patil, N. T., et al., "Palladium-Catalyzed Intramolecular Asymmetric Hydroamination, Hydroalkoxylation, and Hydrocarbonation of Alkynes," Journal of Organic Chemistry, vol. 71, pp. 4270-4279, (2006).
Zhang, Z., et al., "Gold(I)-Catalyzed Intramolecular Enantioselective Hydroalkoxylation of Allenes," Angew. Chem. Int. Ed., vol. 46, pp. 283-285, (2007).
International Search Report issued Oct. 26, 2010 in PCT/JP10/67279 Filed Oct. 1, 2010.

*Primary Examiner* — John Mabry
(74) *Attorney, Agent, or Firm* — Oblon, Spivak, McClelland, Maier & Neustadt, L.L.P.

(57) ABSTRACT

Disclosed are: a ligand for an asymmetric synthesis catalyst; and a process for producing an α-alkenyl cyclic compound using the ligand. Specifically disclosed are: a ligand for an asymmetric synthesis catalyst, which is represented by any one of formulae (1) to (4) [wherein $R^1$ represents —Cl or —Br; $R^2$ represents —$CH_3$ or —$CF_3$; and $R^3$ represents —$CH_2$—CH=$CH_2$ or —H]; and a process for producing an α-alkenyl cyclic compound using the ligand.

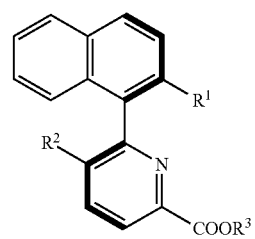

(1)

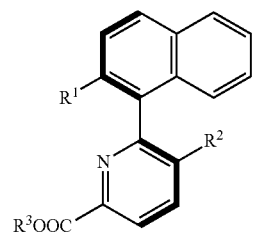

(2)

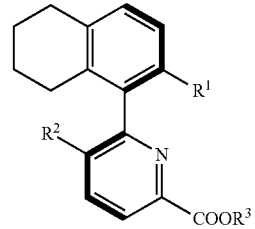

(3)

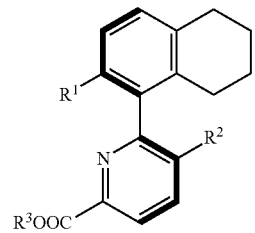

(4)

3 Claims, 2 Drawing Sheets

LIGAND FOR ASYMMETRIC SYNTHESIS CATALYST, AND PROCESS FOR PRODUCTION OF ALPHA-ALKENYL CYCLIC COMPOUND USING THE SAME

CROSS-REFERENCE TO RELATED APPLICATIONS

This application is a National Stage of PCT/JP2010/067279 filed on Oct. 1, 2010. This application is based upon and claims the benefit of priority to Japanese Application No. 2009-233813 filed on Oct. 7, 2009.

BACKGROUND OF THE INVENTION

1. Technical Field

The present invention relates to a ligand for an asymmetric synthesis catalyst and a process for producing an α-alkenyl cyclic compound using the same. More specifically, the present invention relates to a ligand with a specific structure, which can be easily coordinated to Ru possessed by a catalyst precursor and is useful for the production of a chiral α-alkenyl cyclic compound, and a process for producing an α-alkenyl cyclic compound comprising subjecting a specific allyl alcohol to a cyclodehydration reaction in the presence of a catalyst comprising the catalyst precursor and ligand for an asymmetric synthesis catalyst.

2. Background Art

Physiologically active substances include many optically active substances having an asymmetric carbon atom, and it is important to obtain an optically active substance having a predetermined steric structure. As a method for obtaining this optically active substance, indicated is a method comprising synthesizing a racemic substance, and, thereafter, fractionating an optically active substance having a predetermined steric structure, for example, by optical resolution. This method, however, is ineffective, for example, because of the necessity for chemical conversion. Therefore, research and development on an asymmetric synthesis method for selectively synthesizing an optically active substance having a predetermined steric structure are now being promoted.

A cyclic ether having an asymmetric center is indicated as one of the most important structural units in optically active substances such as a polycyclic ether (see, for example, non-patent literature 1). Further, among many basic structures which have hitherto been reported, an α-alkenyl substituted cyclic ether is known to be the most useful. Further, a catalyst having high selectivity especially for the α-alkenyl substituted cyclic ether is drawing attention, and known synthesis methods include the Wacker oxidation type cyclization of an orthoallyl- or homoallyl-phenol derivative (see, for example, non-patent literature 2), the Tsuji-Trost type intramolecular allylation using an ω-hydroxyallyl ester (see, for example, non-patent literature 3), the addition of an alcohol to an alkyne (see, for example, non-patent literature 4), and the addition of an alcohol to an allene (see, for example, non-patent literature 5).

PRIOR TECHNICAL LITERATURE

Non-Patent Literature

Non-patent literature 1: Tetrahedron 1987, 43, 3309-3362
Non-patent literature 2: J. Am. Chem. Soc. 1981, 103, 2318-2323
Non-patent literature 3: Tetrahedron Lett. 1994, 35, 6093-6096
Non-patent literature 4: J. Org. Chem. 2006, 71, 4270-4279
Non-patent literature 5: Angew. Chem. Int. Ed. 2007, 46, 283-285

SUMMARY OF INVENTION

Problem to be Solved by the Invention

The object of the present invention is to provide a ligand with a specific structure, which can be easily coordinated to Ru possessed by a catalyst precursor and is useful for the production of a chiral α-alkenyl cyclic compound, and a process for producing an α-alkenyl cyclic compound comprising subjecting a specific allyl alcohol to a cyclodehydration reaction in the presence of a catalyst comprising the catalyst precursor and ligand for an asymmetric synthesis catalyst.

Means for Solving the Problem

The present invention is as follows.

1. A ligand for an asymmetric synthesis catalyst which is represented by one of the following formulae (1) to (4):

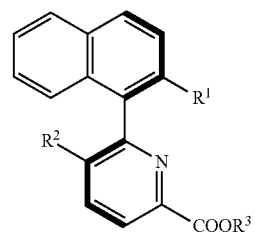

(1)

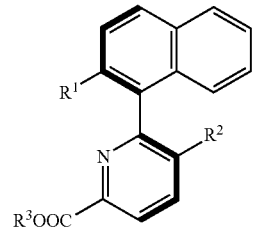

(2)

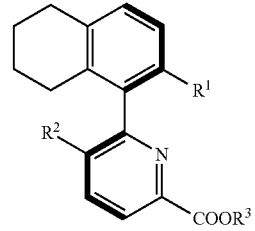

(3)

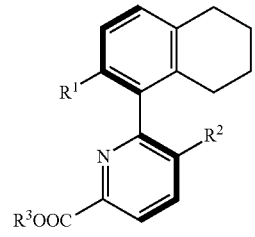

(4)

wherein $R^1$ is —Cl or —Br, $R^2$ is —CH$_3$ or —CF$_3$, and $R^3$ is —CH$_2$—CH=CH$_2$ or —H.

2. The ligand for an asymmetric synthesis catalyst according to 1 above, wherein the ligand is represented by the formula (1) or (2), and wherein $R^1$ is —Cl and $R^2$ is —$CH_3$.

3. A process for producing an α-alkenyl cyclic compound characterized by comprising:

mixing the ligand for an asymmetric synthesis catalyst according to 1 or 2 above and a catalyst precursor represented by the following formula (5), and incorporating one allyl alcohol selected from the group consisting of an ω-hydroxyallyl alcohol represented by the following formula (6), Meldrum's acid type allyl alcohol, a sulfonylamino allyl alcohol and a carboxyallyl alcohol to cause a reaction and obtain a cyclic compound:

[Ru($C_5H_5$)($CH_3CN$)$_3$]$PF_6$      (5)

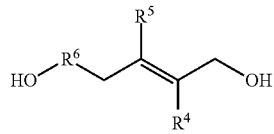

(6)

wherein $R^4$ is —H or an alkyl group having 1 to 5 carbon atoms, $R^5$ is —H or —$CH_3$, and $R^6$ is a divalent organic group.

4. The process for producing an α-alkenyl cyclic compound according to 3 above, wherein the allyl alcohol is the ω-hydroxyallyl alcohol, and wherein the cyclic compound is a cyclic ether having a 5-membered ring ether structure or 6-membered ring ether structure.

5. The process for producing an α-alkenyl cyclic compound according to 4 above, wherein the ω-hydroxyallyl alcohol represented by the formula (6) includes compounds represented by the following (a) to (l):

(a) a compound in which $R^6$ is —$CH_2CH_2CH_2$—, $R^4$ is —H, and $R^5$ is —H in the formula (6);

(b) a compound in which $R^6$ is —$CH_2CH_2$—, $R^4$ is —H, and $R^5$ is —H in the formula (6);

(c) a compound in which $R^6$ is —$CH_2CH_2CH_2$—, $R^4$ is —$CH_3$, and $R^5$ is —H in the formula (6);

(d) a compound in which $R^6$ is —$CH_2CH_2$—, $R^4$ is —$CH_3$, and $R^5$ is —H in the formula (6);

(e) a compound in which $R^6$ is —$CH_2CH_2CH_2$—, $R^4$ is —$C_2H_5$, and $R^5$ is —H in the formula (6);

(f) a compound in which $R^6$ is —$CH_2CH_2CH_2$—, $R^4$ is -n-$C_5H_{11}$, and $R^5$ is —H in the formula (6);

(g) a compound in which $R^6$ is —$CH_2CH_2CH_2$—, $R^4$ is —$CH_2$(i-$C_3H_7$), and $R^5$ is —H in the formula (6);

(h) a compound in which $R^6$ is —$CH_2CH_2CH_2$—, $R^4$ is —H, and $R^5$ is —$CH_3$ in the formula (6);

(i) a compound in which $R^6$ is —C($CH_3$)$_2CH_2CH_2$—, $R^4$ is —H, and $R^5$ is —H in the formula (6);

(j) a compound in which HO—$R^6$ is represented by the following formula (7), $R^4$ is —$CH_3$, and $R^5$ is —H:

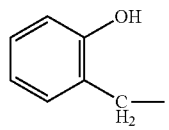

(7)

in the formula (6);

(k) a compound in which HO—$R^6$ is represented by the following formula (8), $R^4$ is —H, and $R^5$ is —$CH_3$:

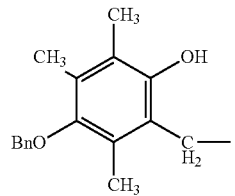

(8)

wherein Bn is a benzyl group, in the formula (6); and (l) a compound in which HO—$R^6$ is represented by the following formula (9), $R^4$ is —$CH_3$, and $R^5$ is —H:

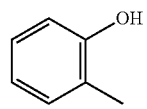

(9)

in the formula (6).

6. The process for producing an α-alkenyl cyclic compound according to any one of 3 to 5 above, wherein the ratio ($M_1$/$M_2$) between the molar number ($M_1$) of the allyl alcohol and the molar number ($M_2$) of the ligand for an asymmetric synthesis catalyst is in a range from 100 to 1,000.

7. The process for producing an α-alkenyl cyclic compound according to any one of 3 to 6 above, wherein the reaction temperature is in a range from 80° C. to 120° C.

8. The process for producing an α-alkenyl cyclic compound according to any one of 3 to 7 above, wherein a reaction solvent is dimethylacetamide.

Effect of the Invention

The ligand for an asymmetric synthesis catalyst according to the present invention can be easily coordinated to Ru possessed by a catalyst precursor having a specific structure to form an asymmetric synthesis catalyst, and the catalyst can be used to subject a specific allyl alcohol to a cyclodehydration reaction to prepare a chiral α-alkenyl cyclic compound in high yield and with high enantioselectivity.

Further, when the ligand for an asymmetric synthesis catalyst is represented by the above formula (1) or (2) wherein $R^1$ is —Cl and $R^2$ is —$CH_3$, it is possible to produce a chiral α-alkenyl cyclic compound in higher yield and with higher selectivity.

According to the process for producing an α-alkenyl cyclic compound according to the present invention, it is possible to subject many types of allyl alcohols to a cyclodehydration reaction with simple operations and steps to easily prepare a chiral α-alkenyl cyclic compound in high yield and with high enantioselectivity.

In addition, when the allyl alcohol is an ω-hydroxyallyl alcohol and the cyclic compound is cyclic ether having a 5-membered ring ether structure or 6-membered ring ether structure, many types of ω-hydroxyallyl alcohols can be used to easily prepare chiral α-alkenyl cyclic compounds in high yield and with high enantioselectivity.

Furthermore, when the ω-hydroxyallyl alcohol represented by the above formula (6) is selected from compounds (a) to (l), it is possible to prepare corresponding various α-alkenyl cyclic ether compounds. The production process according to the present invention has high versatility.

Additionally, when the ratio ($M_1/M_2$) between the mole number ($M_1$) of the allyl alcohol and the molar number ($M_2$) of the ligand for an asymmetric synthesis catalyst ranges from 100 to 1,000, a stable reaction can be made, thereby making it possible to efficiently produce an α-alkenyl cyclic compound in high yield and with high selectivity.

Further, when the reaction temperature ranges from 80° C. to 120° C., an α-alkenyl cyclic compound can be efficiently produced in high yield and with high selectivity, without requiring a long time for the reaction, which provides a practical and useful production process.

In addition, when a reaction solvent is dimethyl acetamide, a stable reaction can be made, thereby making it possible to efficiently prepare an α-alkenyl cyclic compound at high yield and with high selectivity.

MODES FOR CARRYING OUT THE INVENTION

1. Ligand for Asymmetric Synthesis Catalyst

Figure 1:
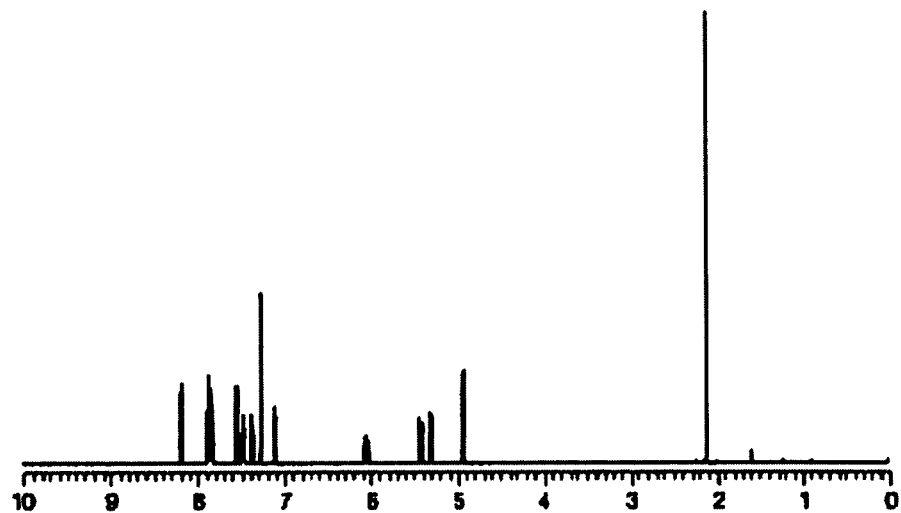
FIG. 1 shows $^1$H-NMR spectrum of allyl 6-(2-chloronaphthalen-1-yl)-5-methylpyridine-2-carboxylate.
Figure 2:
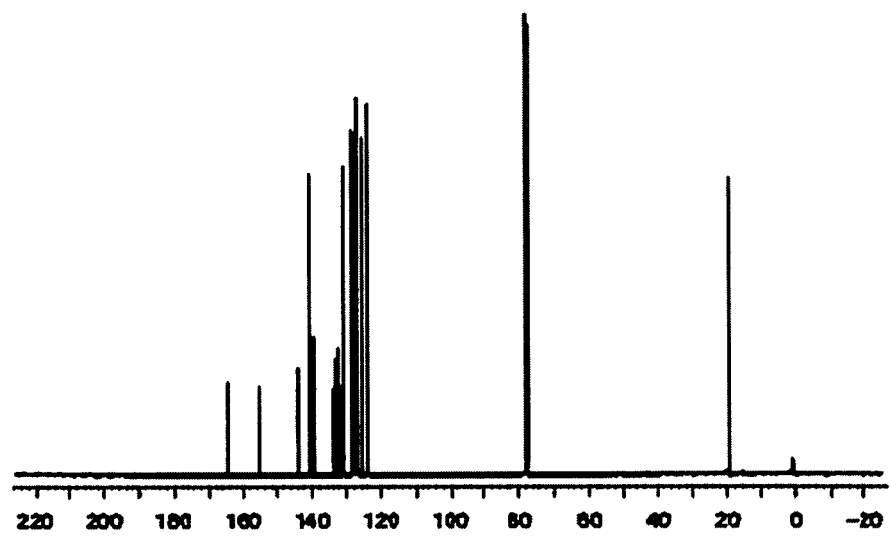
FIG. 2 shows $^{13}$C-NMR spectrum of allyl 6-(2-chloronaphthalen-1-yl)-5-methylpyridine-2-carboxylate.
Figure 3:
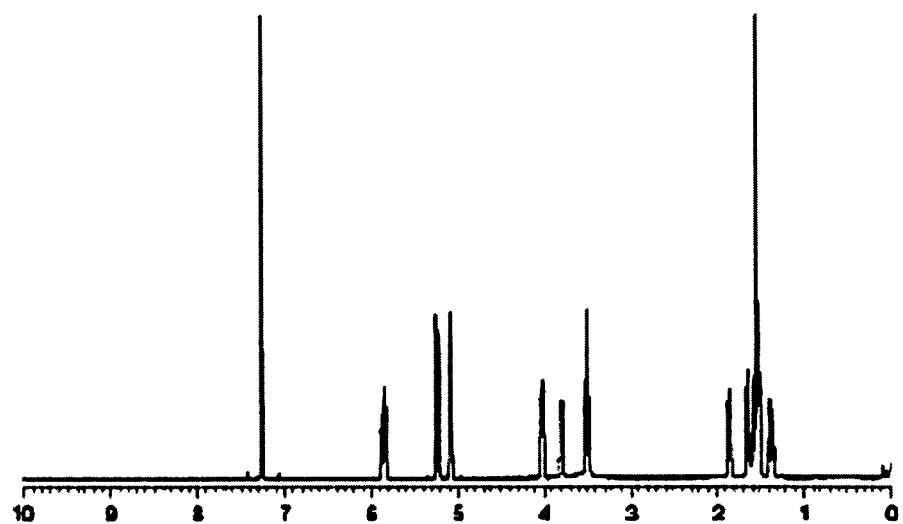
FIG. 3 shows $^1$H-NMR spectrum of α-alkenyl cyclic ether produced by using a compound represented by the above formula (a) as an ω-hydroxyallyl alcohol.
Figure 4:
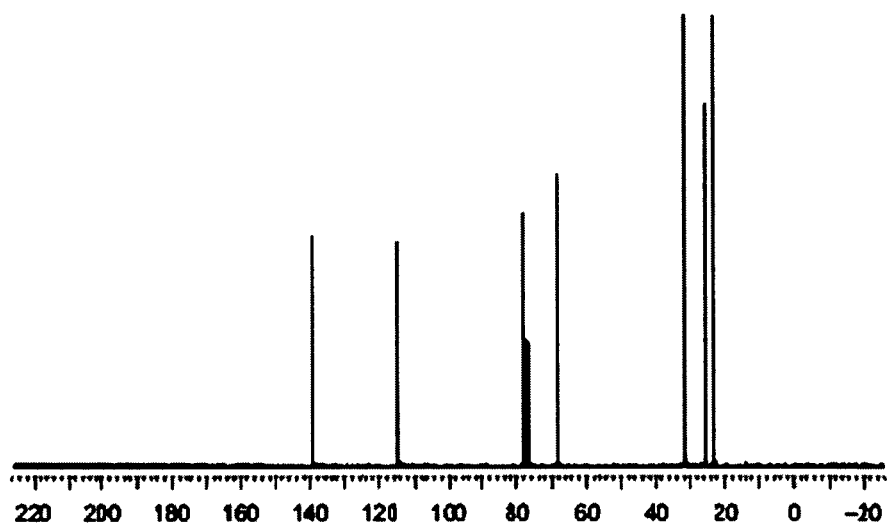
FIG. 4 shows $^{13}$C-NMR spectrum of α-alkenyl cyclic ether produced by using a compound represented by the above formula (a) as an ω-hydroxyallyl alcohol.

The ligand for an asymmetric synthesis catalyst of the present invention (hereinafter as referred to merely as "ligand" in some cases) is represented by one of the above formulae (1) to (4).

In the ligand of formula (1) which is an (R)-substance and the ligand of formula (2) which is an (S)-substance, $R^1$ may be either —Cl (chlorine atom) or —Br (bromine atom), but preferably —Cl. $R^2$ may be either —CH$_3$ (methyl group) or —CF$_3$, but preferably —CH$_3$. Further, $R^3$ may be either —CH$_2$—CH=CH$_2$ (allyl group) or —H (hydrogen atom), but preferably —CH$_2$—CH=CH$_2$. Namely, an allyl ester type ligand is more preferable than an acid type ligand. Therefore, an allyl ester type ligand of formula (1) or (2) wherein $R^1$ is —Cl and $R^2$ is —CH$_3$ is preferred as the ligand.

Also in the ligand of formula (3) which is an (R)-substance and the ligand of formula (4) which is an (S)-substance, $R^1$ is preferably —Cl, $R^2$ is preferably —CH$_3$, and $R^3$ is preferably —CH$_2$—CH=CH$_2$. Namely, an allyl ester type ligand is more preferable than an acid type ligand. Therefore, an allyl ester type ligand of formula (3) or (4) wherein $R^1$ is —Cl and $R^2$ is —CH$_3$ is preferred as the ligand.

The ligand for an asymmetric synthesis catalyst of the present invention is used in combination with a catalyst precursor represented by the above formula (5), namely [Ru (C$_5$H$_5$)(CH$_3$CN)$_3$]PF$_6$ [which can also be represented by the following formula (10) and has a structure portion wherein 3 acetonitrile (CH$_3$CN) molecules are coordinated to Ru] so that a reaction catalyst system is formed. For the ligand and catalyst precursor of the present invention, a solvent may be added to, and mixed with a solid ligand and a solid catalyst precursor for use, a ligand dissolved in a solvent and a solid catalyst precursor may be mixed together for use, a solid ligand and a catalyst precursor dissolved in a solvent may be mixed together for use, or a ligand dissolved in a solvent and a catalyst precursor dissolved in a solvent may be mixed together for use. Further, when solutions in which the respective materials are dissolved are mixed, the solvents for the respective materials may be the same or different. In addition, the ligand produced may be once isolated, and dissolved in a solvent at the time of use, or used as it has been produced, namely, in the state where the ligand is dissolved in the solvent used during production.

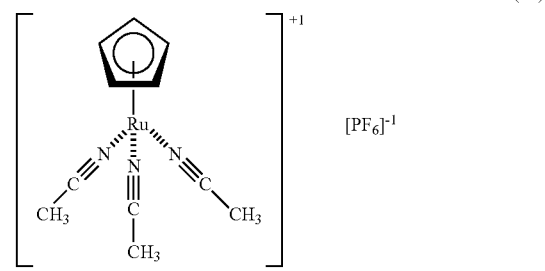

(10)

wherein the dashed lines between Ru and N represent a coordination bond.

2. Preparation of α-Alkenyl Cyclic Compound

The process for producing an α-alkenyl cyclic compound of the present invention comprises mixing a catalyst precursor represented by the above formula (5) [and the above formula (10)] and the ligand for an asymmetric synthesis catalyst of the present invention represented by any one of the above formulae (1) to (4), and, thereafter, incorporating an allyl alcohol (hereinafter also referred to as the "starting material" in some cases) to react them, and producing an α-alkenyl cyclic compound by an intramolecular cyclodehydration reaction of the starting material. For example, when the allyl alcohol is an ω-hydroxyallyl alcohol represented by the above formula (6), an α-alkenyl cyclic ether having a 5-membered ring ether structure or 6-membered ring ether structure can be produced.

In the ω-hydroxyallyl alcohol of the above formula (6) for use in the production of α-alkenyl cyclic ether, $R^4$ may be either —H or an alkyl group having 1 to 5 carbon atoms, but preferably —H. When $R^4$ is an alkyl group, the alkyl group may only have 1 to 5 carbon atoms, but is preferably —CH$_3$ having 1 carbon atom or —C$_2$H$_5$ (ethyl group) having 2 carbon atoms, and, especially, more preferably —CH$_3$ having 1 carbon atom. Further, the alkyl group may be a linear alkyl group or a branched alkyl group. Further, $R^5$ may be either —H or —CH$_3$, but preferably —H. Further, $R^6$ is a divalent organic group in which the oxygen atom possessed by the hydroxyl group at w position binds to the carbon atom to which $R^5$ binds to form a 5-membered ring ether structure or a 6-membered ring ether structure.

The ω-hydroxyallyl alcohol used as the starting material is not especially limited so long as it has $R^4$, $R^5$ and $R^6$ as defined above and can provide α-alkenyl cyclic ether having a 5-membered ring ether structure or 6-membered ring ether structure, and various starting materials can be used. In order to provide α-alkenyl cyclic ether having a 5-membered ring ether structure or 6-membered ring ether structure, the usable starting material includes ω-hydroxyallyl alcohols of formula (6) wherein $R^6$ is a structural portion represented by —CH$_2$CH$_2$—, —CH$_2$CH$_2$CH$_2$— or —C(CH$_3$)$_2$CH$_2$CH$_2$—, and wherein HO—$R^6$ is a structural portion represented by the above formula (7), (8) or (9).

Meldrum's acid type allyl alcohol, a sulfonylamino allyl alcohol and a carboxyallyl alcohol can also be used as the allyl alcohol. As is the case with the ω-hydroxyallyl alcohol, an α-alkenyl cyclic compound can be produced by an intramolecular cyclodehydration reaction of the starting material. In this way, in the process for producing an α-alkenyl cyclic compound according to the present invention, an allyl alcohol having a substituent with a hydrogen atom and at least one atom of an oxygen atom, a nitrogen atom, a sulfur atom and a carbon atom is used as the starting material. The hydrogen atom possessed by the substituent and the hydroxyl group are reacted to produce an α-alkenyl cyclic compound by cyclodehydration.

In the case of the Meldrum's acid type allyl alcohol, the substituent has a hydrogen atom, an oxygen atom and a carbon atom, and the hydrogen atom involved in a dehydration reaction binds to the carbon atom. In the allyl alcohol, an intramolecular cyclodehydration reaction is promoted in a reaction system employing the ligand for an asymmetric synthesis catalyst of the present invention and a specific catalyst precursor, thereby making it possible to efficiently produce an α-alkenyl cyclic compound. Further, the moiety which binds to the carbon atom in the skeleton portion except the substituent may be either the hydrogen atom or the alkyl group in the allyl alcohol.

In the case of the sulfonylamino allyl alcohol, the substituent has a hydrogen atom, a nitrogen atom, a sulfur atom and an oxygen atom, and the hydrogen atom involved in a dehydration reaction binds to the nitrogen atom. In the allyl alcohol, an intramolecular cyclodehydration reaction is promoted in a reaction system employing the ligand for an asymmetric synthesis catalyst of the present invention and a specific catalyst precursor, thereby making it possible to efficiently produce an α-alkenyl cyclic compound. Further, in the allyl alcohol, the moiety which binds to the carbon atom in the skeleton portion except the substituent may be either the hydrogen atom or the alkyl group.

In the case of the carboxyallyl alcohol, the substituent has a hydrogen atom, an oxygen atom and a carbon atom, and the hydrogen atom involved in a dehydration reaction binds to the oxygen atom. In the allyl alcohol, an intramolecular cyclodehydration reaction is promoted in a reaction system employing the ligand for an asymmetric synthesis catalyst of the present invention and a specific catalyst precursor, thereby making it possible to efficiently produce an α-alkenyl cyclic compound. Further, in the allyl alcohol, the moiety which binds to the carbon atom in the skeleton portion except the substituent may be either the hydrogen atom or the alkyl group.

In the process for producing an α-alkenyl cyclic compound according to the present invention, a ligand for an asymmetric synthesis catalyst and a catalyst precursor are mixed to form an asymmetric synthesis catalyst, and, thereafter, the catalyst is reacted with a starting material to be incorporated to prepare an α-alkenyl cyclic compound. A method for mixing the ligand and the catalyst precursor is not especially limited, but a mixing method comprising adding a solution in which the ligand is dissolved to a solid catalyst precursor introduced into a reactor is preferred. The starting material is produced as a liquid or solid stereoisomer, and dissolved in an appropriate solvent at the time of use. Additionally, the solution in which the starting material is dissolved is incorporated into a solution in which a catalyst system has been formed by the ligand and the catalyst precursor, thereby producing an α-alkenyl cyclic compound.

While the solvent for dissolving the ligand and the solvent for dissolving the catalyst precursor may be the same or different, as described above, the solvent for dissolving the starting material may also be the same as, or different from, at least one of the solvent for dissolving the catalyst precursor and the solvent for dissolving the ligand. Examples of the solvent include dimethylacetamide (DMA), dimethylformamide (DMF), tetrahydrofuran (THF), cyclopentylmethylether (CPME), dioxane, dichloromethane, acetone, toluene, methyl alcohol, ethyl alcohol, t-butyl alcohol, i-propyl alcohol, acetic acid, water, and the like.

Among the above solvents, dichloromethane, acetone and the like are preferred as the solvents for dissolving the catalyst precursor and the ligand, respectively. DMA, DMF, THF, CPME, t-butyl alcohol and the like are preferred as the solvent for dissolving the starting material, normally, the solvent serving as a reaction solvent, and DMA is more preferably used.

While the ratio ($M_1/M_2$) between the molar number ($M_1$) of the starting material and the molar number ($M_2$) of the ligand is not especially limited so long as an α-alkenyl cyclic compound of interest can be produced, a ratio which provides a rate of conversion from the starting material to an α-alkenyl cyclic compound is 90% or more, especially 95% or more, and further 99% or more is preferred from the viewpoint of practicality. Specifically, the ratio ($M_1/M_2$) preferably ranges from 50 to 5,000, especially from 70 to 3,000, and further from 100 to 1,000. Thus, in the process for producing an α-alkenyl cyclic compound according to the present invention, the conversion rate can be sufficiently enhanced by a very small amount of catalyst as compared with conventional methods.

Further, the reaction condition is not especially limited in the process for producing an α-alkenyl cyclic compound according to the present invention, and is preferably controlled as appropriate depending, for example, on the types of the ligand and the starting material, especially, the type of the starting material. The reaction temperature is determined depending on the reaction period of time, but is preferably defined as 50° C. to 150° C., especially 70° C. to 130° C., and further 80° C. to 120° C. from the viewpoint of practicality. The reaction period of time can be defined as 0.1 hour to 3 hours, and especially 0.1 hour to 1.5 hours if the reaction temperature ranges from 80° C. to 120° C. When the reaction temperature is a low temperature which is less than 80° C., the reaction period of time can be prolonged, thereby sufficiently increasing the rate of conversion from the starting material to an α-alkenyl cyclic compound to 99% or more.

The atmosphere during the reaction is an inert atmosphere, and the inert atmosphere is not especially limited, but can be a nitrogen gas atmosphere or a rare gas atmosphere such as argon gas, helium gas or neon gas. Further, in the process for producing an α-alkenyl cyclic compound according to the present invention, the target α-alkenyl cyclic compound can be recovered and purified by conventionally known methods, for example, methods including distillation, adsorption, extraction and recrystallization, or by a combined method of these methods, after completion of the reaction. The target optically active substance can further be purified, for example, by optical resolution, according to need.

In the present invention, the mechanism for producing an α-alkenyl cyclic compound by forming a catalyst system using a ligand and a catalyst precursor and incorporating a specific allyl alcohol into the catalyst system to react them is considered to be as defined as follows, when the allyl alcohol is, for example, an ω-hydroxyallyl alcohol:

(R)—Cl-Naph-PyCOOH which is a ligand of the acid type according to the formula (1) forms a complex together with [CpRu(CH$_3$CN)$_3$]PF$_6$ (catalyst precursor) to form [CpRu((R)—Cl-Naph-PyCOOH)]PF$_6$, which captures an allyl alcohol substrate to form a sub/cat complex (starting material/catalyst complex) [see the following formula (11)]. Here, the electrophilicity of the γ carbon is significantly improved by a hydrogen bond between the proton of the carboxylic acid in the ligand and the hydroxy group in the ω-hydroxyallyl alcohol. Further, a π-allyl complex (R, R$_{Ru}$)-Asyn,anti [see the following formula (12)] (wherein the "syn" represents a positional relation between the proton at position 2 and the substituent at position 3 in the π-allyl; and the "anti" represents a positional relation between the carboxylate ligand and the substituent at position 3 in the π-allyl) is exothermically formed together with the improvement in nucleophilicity of the central ruthenium (II) atom due to high electron donating property of the sp$^2$ nitrogen atom and cyclopentadienyl group of the ligand. The π-allyl complex is isomerized into a more stable (R,R$_{Ru}$)-Asyn,syn substance [see the following formula (13a)] from steric repulsion between the substituent at position 3 in the π-allyl and the ligand naphthalene portion. Further, an S-product [see the following formula (13c)] is obtained if the ω-hydroxy group necleophilically attacks the π-allyl carbon from the inside, and an R-product [see the following formula (13d)] is obtained if the ω-hydroxy group necleophilically attacks the π-allyl carbon from the outside. In this way, it is considered that the inside attack which enables a hydrogen bond of the ω-hydroxy proton with the oxygen atom in the carboxylate ligand is given priority so that an (R)—Naph-PyCOOH/CpRu catalyst provides an S-product. It cannot be denied that an S-product is produced by the outside attack via (R,S$_{Ru}$)Asyn,syn diastereomers. Further, while the stability between two diastereomer intermediates would be determined by the balance, for example, of the stereo repulsion among the Cp part on the Ru atom, the π-allyl part and the PyCOO part, the hydrogen bond between CpH/Cl and the CH-π interaction between benzene ring/CpH, the (R,R$_{Ru}$)-Asyn,syn substance [see the following formula (13a)] which enables a hydrogen bond between CpH and the Cl atom is considered to be more beneficial than the (R,S$_{Ru}$)-Asyn,syn substance [see the following formula (13b)].

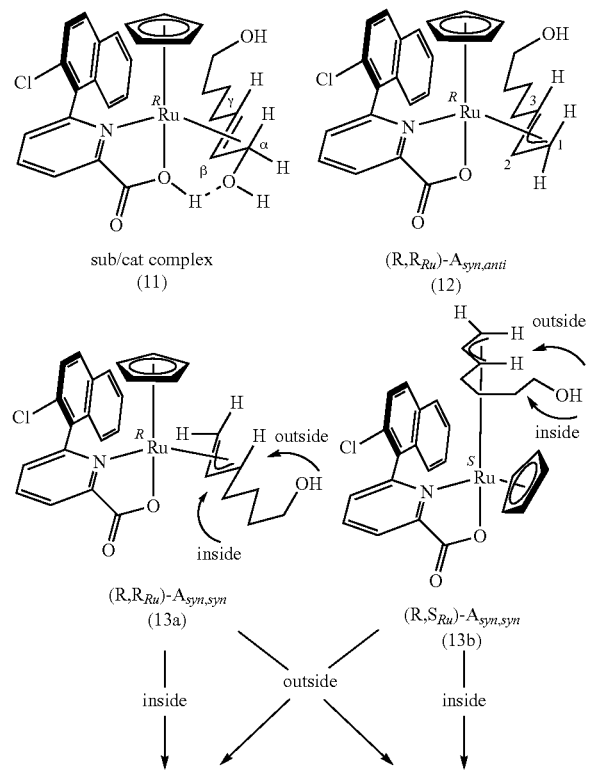

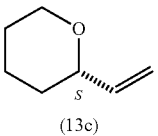

(13c)

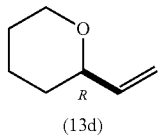

(13d)

EXAMPLES

Example 1

Production of allyl 6-(2-chloronaphthalen-1-yl)-5-methylpyridine-2-carboxylate (1) Preparation of 2-(2-chloronaphthalen-1-yl)-3-methylpyridine Into a dried Schlenk tube having a volume of 250 mL, 8 g (24 mmol) of 2-(2-triethylsilyl)naphthalen-1-yl)-3-methylpyridine and 48 mL of dichloromethane were introduced, and the temperature cooled to −78° C. Then, 12.7 mL (28.2 mmol) of a 2.27 M-concentration toluene solution of boron chloride was added, and the solution was stirred in a sealed system at the same temperature for 30 minutes. Thereafter, all volatile contents were removed under reduced pressure. Then, 48 mL of methanol, 48 mL of water and 9.6 g (71.6 mmol) of copper chloride were added to the brownish yellow residue, and the tube was sealed with a cold finger. The mixture was increased in temperature and refluxed for 48 hours. Next, the mixture was cooled to room temperature, and the entire mixture was separated into 50 mL of an ether layer and 50 mL of a 5M-concentration ammonia water layer. Extraction from the water layer was conducted by using 50 mL of ether three times, and the entire ether layer was mixed, and washed with 50 mL of salt water. Then, the layer was dried with 50 g of sodium sulfate, and subjected to dehydration and filtration steps to obtain 6 g of a yellow oily product. This oily product was then purified by silica gel chromatography (250 g; the solvent used was a solvent mixture of hexane and ethyl acetate in a mass ratio of 4:1), thereby obtaining 5.66 g (yield: 93%) of pale yellow 2-(2-chloronaphthalen-1-yl)-3-methylpyridine.

(2) Preparation of 6-(2-chloronaphthalen-1-yl)-5-methylpyridine-2-carbonitrile

A round-bottomed flask having a volume of 50 mL and equipped with a glass stopper and a three-way cock was dried, and 890 mg (3.51 mmol) of 2-(2-chloronaphthalen-1-yl)-3-methylpyridine and 20 mL of dichloromethane were introduced thereinto. This colorless solution was cooled to 0° C., and then 1.59 g (69-75%) of m-CPBA (meta-chloroperbenzoic acid) was each added thereto three times at intervals of 10 minutes. Next, the temperature was slowly increased to room temperature, and the colorless solution was stirred for 2 hours. Thereafter, the solution was cooled to 0° C. again, and 10 mL of an aqueous NaOH solution having a concentration of 1M was gradually added. Thereafter, an organic layer was washed with 10 mL of an aqueous NaOH solution having a concentration of 1M and 10 mL of salt water, then dried with 50 g of sodium sulfate, and subjected to dehydration and filtration steps, thereby obtaining 947 mg of yellow oily 2-(2-chloronaphthalen-1-yl)-5-methylpyridine-1-oxide.

Next, 889 mg (3.29 mmol) of an N-oxide compound, 10 mL of dichloromethane and 362 μL (3.94 mmol) of N,N- dimethylcarbamoylchloride were introduced in this order into a dried Schlenk tube having a volume of 100 mL. The mixture was left at rest at room temperature for 30 minutes, and 807 μL (6.58 mmol) of $(CH_3)_3SiCN$ was added thereto. Then, a reflux condenser was attached to the Schlenk tube, and the mixture was stirred at 60° C. for 12 hours. Thereafter, the mixture was cooled to room temperature, and poured into a separation funnel in which 10 mL of dichloromethane and 10 mL of a saturated aqueous solution of sodium hydrogen carbonate were put. Then, an organic layer was washed with 10 mL of an aqueous NaOH solution having a concentration of 1 M and 10 mL of salt water, then dried with 5 g of sodium sulfate, and subjected to dehydration and filtration steps, thereby obtaining a yellow oily product. Next, this oily product was purified by silica gel column chromatography (100 g; the solvent used was a solvent mixture of hexane and ethyl acetate in a mass ratio of 5:1) to obtain 856 mg (yield: 93%) of 6-(2-chloronaphthalen-1-yl)-5-methylpyridine-2-carbonitrile.

(3) Production of allyl 6-(2-chloronaphthalen-1-yl)-5-methylpyridine-2-carboxylate Into a dried Schlenk tube having a volume of 50 mL, 800 mg (2.87 mmol) of 6-(2-chloronaphthalen-1-yl)-5-methylpyridine-2-carbonitrile and 5 mL of an aqueous hydrochloric acid solution having a concentration of 12 M were introduced. A spiral cooler was attached to the tube, and the mixture was refluxed in a released system for 12 hours. Then, the mixture was cooled to room temperature, and all volatile contents were removed under reduced pressure. Then, 4 mL of $SOCl_2$ was added to the resultant yellow solid under an Ar gas stream. The mixture was stirred at room temperature in a sealed system for 1 hour, and concentrated under reduced pressure. Next, 4 mL of an allyl alcohol was added, and the mixture was stirred for 5 hours for concentration. The residue was dissolved in 20 mL of dichloromethane, washed twice with 10 mL of an aqueous $NaHCO_3$ solution having a saturation concentration, further washed with 10 mL of salt water, then dried with 5 g of sodium sulfate, and subjected to dehydration and filtration steps to obtain a white solid. This white solid was purified by silica gel column chromatography (50 g; the solvent used was a solvent mixture of ethyl acetate and hexane in a mass ratio of 1:8), thereby obtaining 800 mg of white solid allyl 6-(2-chloronaphthalen-1-yl)-5-methylpyridine-2-carboxylate (yield: 83%). This white solid product contains ligands for an asymmetric synthesis catalyst represented by formulae (1) and (2).

(4) Separation of Racemic Substance Produced in Above (3)

The racemic substance produced in the above (3) was separated into an (R)-substance and an (S)-substance by high-performance liquid chromatography [column: "CHIRALCEL OD-H" (manufactured by Daicel Corporation, φ2 cm×25 cm); solvent: solvent mixture consisting of hexane and 2-propanol in a mass ratio of 10:1; flow rate: 8 mL/min.; and wavelength of light source: 254 nm] [the (R)-substance and (S)-substance showed peaks at positions of 50.1 min. and 76.0 min., respectively]. The optical purity of the respective separated enantiomers was confirmed by high-performance liquid chromatography [column: "CHIRALCEL OD-H" (manufactured by Daicel Corporation, φ0.46 cm×25 cm); solvent: solvent mixture consisting of hexane and 2-propanol in a mass ratio of 5:1; flow rate: 1 mL/min.; and wavelength of light source: 254 nm] [the (R)-substance and (S)-substance showed peaks at positions of 14.1 min. and 25.0 min., respectively].

(5) Confirmation of Structure

It was confirmed, by X-ray crystal structural analysis using a menthyl ester of the (S)-substance which showed a peak at a position of 76.0 min. in the high-performance liquid chromatography in the above (4), that the resultant white solid product was allyl 6-(2-chloronaphthalen-1-yl)-5-methylpyridine-2-carboxylate. $^1$H-NMR spectrum of the product was measured by means of "JEOL JMN ECA 600 (600 MHz) spectrometer", and $^{13}$C-NMR spectrum was measured by means of the "same (152 MHz) spectrometer" under complete proton decoupling. The spectrum data is shown as follows. It could be confirmed, also from this spectrum data, that allyl 6-(2-chloronaphthalen-1-yl)-5-methylpyridine-2-carboxylate of interest had been obtained.

$^1$H NMR (CDCl$_3$) δ 2.08 (s, 3H, CH$_3$), 4.89 (d, J=5.51 Hz, 2H, OCH$_2$), 5.26 (dd, J=1.38, 10.33 Hz, $^1$H, CH=CHH), 5.38 (dd, J=1.38, 17.21 Hz, 1H, CH=CHH), 6.00-6.08 (m, 1H, CH=CH$_2$), 7.09 (d, J=8.26 Hz, 1H, ar), 7.36 (dd, J=6.89, 8.26 Hz, 1H, ar), 7.46 (dd, J=7.57, 7.57 Hz, 1H, ar), 7.52 (d, J=8.95 Hz, 1H ar), 7.80-7.87 (m, 3H, ar), 8.17 (d, J=7.57 Hz, 1H, ar); $^{13}$C NMR (CDCl$_3$) δ 18.7, 66.3, 118.7, 124.7, 125.1, 126.1, 127.1, 127.2, 128.1, 129.8, 130.8, 132.07, 132.13, 132.8, 134.8, 137.6, 138.5, 146.0, 156.5, 164.9; HRMS m/z (M$^+$) obsd 337.0882, calcd for C$_{20}$H$_{16}$ClNO$_2$ 337.0870.

(6) Preparation of 6-(2-chloronaphthalen-1-yl)-5-methylpyridine-2-carboxylic acid Ligands of the acid types of the formulae (1) and (2) were prepared by hydrolyzing the allyl ester type of the formula (1) and the allyl ester type of the formula (2) obtained by separating the racemic substance of allyl ester in the above (4) as follows.

Into a dried Schlenk tube having a volume of 10 mL, a solvent mixture of ethanol, water and ether in equivalent amounts was introduced, and 7.80 mg (185 μmol) of solid lithium hydroxide (LiOH.H$_2$O) was added thereto. The mixture was stirred at room temperature for 30 minutes. Then, the mixture was separated into 10 mL of water and 10 mL of ether, and extraction from the ether layer was conducted three times by means of 5 mL of water. Subsequently, 0.5 mL of acetic acid was added to the entire water layer, and extraction was conducted three times by means of 10 mL of dichloromethane. Then, the entire organic layer was dried with 3 g of sodium sulfate, and subjected to dehydration and filtration steps, thereby obtaining 39.0 mg (yield: 98%) of 6-(2-chloronaphthalen-1-yl)-5-methylpyridine-2-carboxylic acid as a colorless oily product.

For comparison, a ligand wherein —Cl is replaced by —CH$_3$ in the ligand of the allyl ester type of the formula (1) and a ligand wherein —Cl is replaced by a phenyl group in the ligand of the allyl ester type of the formula (1) were produced. The ligand wherein —Cl is replaced by —CH$_3$ in the ligand of the allyl ester type of the formula (1) was produced by a synthetic method via 3-methyl-2-(2-methylnaphthalen-1-yl)pyridine and 5-methyl-6-(2-methylnaphthalen-1-yl)pyridine-2-carbonitrile. Further, the ligand wherein —Cl is replaced by a phenyl group in the ligand of the allyl ester type of the formula (1) was produced by a synthetic method via 3-methyl-2-(2-phenylnaphthalen-1-yl)pyridine and 5-methyl-6-(2-phenylnaphthalen-1-yl)pyridine-2-carbonitrile. Further, the racemic substances of the respective ligands were separated into an (R)-substance and an (S)-substance by high-performance liquid chromatography, as is the case with the ligand of the present invention.

Example 2

Production of α-alkenyl Cyclic Ether

Experimental Examples 1 to 3

Into a dried 50 mL-volume Schlenk tube with a Young valve, which was filled with Ar and in which a magnetic stirring rod was put, 4.34 mg (10.0 μmol) of a catalyst precursor represented by the formula (5) was introduced. Then, 1.00 mL of the ligand produced in Example 1 [acid type of the formula (1) (Experimental Example 1) and acid type of the formula (2) (Experimental Example 2) as well as allyl ester type of the formula (1) (Experimental Example 3), as shown in Table 1] (A 10.0 mM-concentration dichloromethane solution was used. Thus, the amount of the ligand was 10.0 μmol.) was added by means of a hermetically sealed syringe. Next, the solution was carefully concentrated under reduced pressure, and 10.0 mL of the above compound (a) as a starting material (A 100 mM-concentration DMA solution was used and the amount of the starting material was accordingly 10.0 mmol.) was added to the resultant yellow solid at room temperature, and the temperature was increased to 100° C. The tube was sealed, and the mixture was stirred at the same temperature for 1 hour to produce α-alkenyl cyclic ether represented by the following the formula (14).

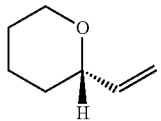

(14)

(1) Conversion Rate

The reaction mixture was cooled to room temperature, and was used in an amount of 1 μL to obtain the conversion rate by gas chromatography analysis [column: "J&W Scientific DB-5" (0.25 mm×0.25 μm×30 m); temperature: held at 50° C. for 10 minutes and then increased to 200° C. at 10° C./min.; 140 kPa; no sprit].

(2) Enantioselectivity

The reaction mixture was cooled to room temperature, and was used in an amount of 1 μL to conduct gas chromatography analysis [column: "CHIRALDEX G-BP" (0.25 mm×0.125 μm×30 m); temperature: held at 40° C. for 10 minutes, then increased to 100° C. at 10° C./min. and held at this temperature for 20 minutes; 140 kPa; sprit ratio: 100:1] to obtain enantioselectivity (er) [(S)-substance/(R)-substance] based on the peak area ratio between the (S)-substance and (R)-substance.

(3) Confirmation of Structure

The structure of the main product, (S)-substance, was confirmed by X-ray crystal structural analysis using a camphanic ester of tetrahydro-2H-pyran-2-ylmethanol obtained by ozone degradation and $NaBH_4$ reduction of this (S)-substance. It could be confirmed, also from the spectrum data obtained by measuring $^1$H-NMR spectrum and $^{13}$C-NMR spectrum in the same manner as described above, that the target α-alkenyl cyclic ether represented by the formula (14) had been obtained.

$^1$H NMR ($CDCl_3$) δ 1.34-1.42 (m, 1H, CHH), 1.49-1.63 (m, 3H, $CH_2$ and CHH), 1.64-1.69 (m, 1H, CHH), 1.83-1.88 (m, 1H, CHH), 3.49 (dt, J=2.07, 11.71 Hz, 1H, CHHO), 3.77-3.82 (m, 1H, CHHO), 4.00-4.04 (m, 1H, OCH), 5.09 (d, J=11.02 Hz, 1H, CH=CHH), 5.22 (d, J=17.21 Hz, 1H, CH=CHH), 5.85 (ddd, J=5.51, 11.02, 17.56 Hz, 1H, CH=$CH_2$); $^{13}$C NMR ($CDCl_3$) δ 23.3, 25.8, 31.8, 68.3, 78.2, 114.5, 139.5; HRMS m/z (M$^+$) obsd 112.0849, calcd for $C_7H_{12}O$ 112.0888 (out of the error range ±5 ppm because of low molecular weight).

A compound (a), which was an ω-hydroxyallyl alcohol used as a starting material for producing an α-alkenyl cyclic ether, was produced as follows.

The corresponding α,β-unsaturated ester was used for Horner-Wadsworth-Emmons conversion between the carbon atom at position 2 and the carbon atom at position 3, and, thereafter, the target compound was synthesized by a conventionally known DIBAL-H conversion method. Steric isomers were separated by silica gel column chromatography at the stage of the α,β-unsaturated ester.

Compounds (b) to (l), which were ω-Hydroxyallyl alcohols used as starting materials in Example 4 described below and a compound having one more methylene group possessed by $R^6$ than that of the compound (a) were produced for Comparative Example in the same manner.

Example 3

Experimental Examples 4 to 22

Various conditions were varied as shown in Table 1, utilizing Example 2, to produce α-alkenyl cyclic ethers represented by the formula (14).

Experimental Example 4: similar to Experimental Example 3 except that the concentration of the starting material was defined as 1,000 mM and that the ligand concentration was defined as 10 mM.

Experimental Example 5: similar to Experimental Example 3 except that the ligand concentration was defined as 0.1 mM, namely, the amount of the catalyst was decreased to 1/10.

Experimental Example 6: similar to Experimental Example 3 except that the concentration of the starting material was defined as 1,000 mM, namely, the amount of the starting material was decoupled, and that the ligand used was the allyl ester type of the formula (2).

Experimental Example 7: similar to Experimental Example 3 except that the reaction temperature was defined as 50° C.

Experimental Example 8: similar to Experimental Example 3 except that the solvent used was DMF.

Experimental Example 9: similar to Experimental Example 3 except that the solvent used was $CH_3CN$.

Experimental Example 10: similar to Experimental Example 3 except that the solvent used was acetone.

Experimental Example 11: similar to Experimental Example 3 except that the solvent used was THF.

Experimental Example 12: similar to Experimental Example 3 except that the solvent used was CPME.

Experimental Example 13: similar to Experimental Example 3 except that the solvent used was dioxane.

Experimental Example 14: similar to Experimental Example 3 except that the solvent used was $CH_2Cl_2$.

Experimental Example 15: similar to Experimental Example 3 except that the solvent used was toluene.

Experimental Example 16: similar to Experimental Example 3 except that the solvent used was t-$C_4H_9OH$.

Experimental Example 17: similar to Experimental Example 16 except that the concentration of the starting material was defined as 1,000 mM, namely, the mass thereof was decoupled.

Experimental Example 18: similar to Experimental Example 3 except that the solvent used was i-C₃H₇OH.

Experimental Example 19: similar to Experimental Example 3 except that the solvent used was C₂H₅OH.

Experimental Example 20: similar to Experimental Example 3 except that the solvent used was CH₃OH.

Experimental Example 21: similar to Experimental Example 3 except that the solvent used was H₂O.

Experimental Example 22: similar to Experimental Example 3 except that the solvent used was CH₃COOH.

Conversion rates and enantioselectivities for Experimental Examples 4 to 22 were obtained in the same manner as described above.

Results of Examples 2 and 3 are indicated together in Table 1.

In the meantime, as Comparative Examples, produced were α-alkenyl cyclic ethers of, Experimental Example 23 wherein reaction was carried out in the same manner as those in Experimental Example 3 expect that the ligand used was a ligand wherein —Cl is replaced by —CH₃ in the allyl ester type of the formula (1), Experimental Example 24 wherein the concentration of the ligand was changed to 0.1 mM in this Experimental Example 23, and Experimental Example 25 wherein the reaction was carried out in the same manner as those in Experimental Example 3 expect that the ligand used was a ligand wherein —Cl is replaced by a phenyl group in the allyl ester type of the formula (1). Conversion rates in Experimental Examples 23 to 25 and enantioselectivity in Experimental Example 23 were obtained in the same manner as described above. The production conditions and results for Examples 23 to 25 are indicated together in Table 1.

According to the results shown in Table 1, it is seen that the conversion rate is 99% or more both in Experimental Example 1 using the acid type of the formula (1) as the ligand and DMA as the solvent, and in Experimental Example 2 using the acid type of the formula (2) as the ligand and DMA as the solvent, that "er" are respectively 97:3 and 3:97, and thus that both the conversion rate and the selectivity are high. Similarly excellent results were obtained in all of Experimental Example 3 using the allyl ester type of the formula (1), Experimental Example 4 wherein both the starting material and the ligand had a concentration 10 times higher than those employed in Experimental Example 3, Experimental Example 5 wherein the amount of the catalyst was decreased to ¹/₁₀ in Experimental Example 3, and Experimental Example 6 wherein the ligand used was changed to the allyl ester type of the formula (2), the amount of the catalyst was unchanged and the amount of the starting material was increased by 10 times in Experimental Example 3. Thus, it is understood that, even when the amount of the catalyst is very small with respect to that of the starting material, both the conversion rate and the selectivity are sufficiently high. Further, the selectivity was high, but the conversion rate was decreased in Experimental Example 7 wherein the reaction temperature was changed to 50° C. in Experimental Example 3. However, a 5-hour reaction improved the conversion rate to 99% or more.

Additionally, equivalent excellent conversion rates and selectivities were obtained in Experimental Examples 8, 11 and 12 employing respectively DMF, THF, and CPME as a highly polar solvent. However, it is understood that Experimental Examples 10, 13 and 14 employing respectively acetone, dioxane and CH₂Cl₂ show a high conversion rate, but have a tendency that selectivities are decreased, and that Experimental Example 15 employing toluene has a tendency that both the conversion rate and the selectivity are decreased.

TABLE 1

| Experimental Example | Starting Material [Concentration: mM] | Ligand [type/concentration: mM] | Solvent | Conversion rate [%] | er |
|---|---|---|---|---|---|
| 1 | 100 | formula (1), Acid type/1 | DMA | >99 | 97:3 |
| 2 | 100 | formula (2), Acid type/1 | DMA | >99 | 3:97 |
| 3 | 100 | formula (1), ES type/1 | DMA | >99 | 97:3 |
| 4 | 1,000 | formula (1), ES type/10 | DMA | >99 | 97:3 |
| 5 | 100 | formula (1), ES type/0.1 | DMA | >99 | 97:3 |
| 6 | 1,000 | formula (2), ES type/1 | DMA | >99 | 3:97 |
| *7 | 100 | formula (1), ES type/1 | DMA | 74 | 97:3 |
| 8 | 100 | formula (1), ES type/1 | DMF | >99 | 97:3 |
| 9 | 100 | formula (1), ES type/1 | $CH_3CN$ | 7 | 73:27 |
| 10 | 100 | formula (1), ES type/1 | Acetone | >99 | 80:20 |
| 11 | 100 | formula (1), ES type/1 | THF | >99 | 95:5 |
| 12 | 100 | formula (1), ES type/1 | CPME | >99 | 95:5 |
| 13 | 100 | formula (1), ES type/1 | Dioxane | >99 | 72:28 |
| 14 | 100 | formula (1), ES type/1 | $CH_2Cl_2$ | >99 | 81:19 |
| 15 | 100 | formula (1), ES type/1 | Toluene | 78 | 87:13 |
| 16 | 100 | formula (1), ES type/1 | $t\text{-}C_4H_9OH$ | >99 | 92:8 |
| 17 | 1,000 | formula (1), ES type/1 | $t\text{-}C_4H_9OH$ | >99 | 92:8 |
| 18 | 100 | formula (1), ES type/1 | $i\text{-}C_3H_7OH$ | 98 | 91:9 |
| 19 | 100 | formula (1), ES type/1 | $C_2H_5OH$ | 92 | 85:15 |
| 20 | 100 | formula (1), ES type/1 | $CH_3OH$ | 95 | 76:24 |
| 21 | 100 | formula (1), ES type/1 | $H_2O$ | >99 | 77:23 |
| 22 | 100 | formula (1), ES type/1 | $CH_3COOH$ | >99 | 65:35 |
| 23 | 100 | formula (1), ES type (Cl → $CH_3$)/1 | DMA | 70 | 9:91 |
| 24 | 100 | formula (1), ES type (Cl → $CH_3$)/0.1 | DMA | 3 | — |
| 25 | 100 | formula (1), ES type (Cl → phenyl)/1 | DMA | 3 | — |

*7: Reaction temperature: 50° C.;
ES type means allyl ester type.

In addition, the reaction is almost stopped in Experimental Example 9 employing CH$_3$CN as the solvent. This phenomenon is considered to be caused since the catalyst precursor has a structure wherein 3 acetonitrile (CH$_3$CN) molecules are coordinated to Ru. Further, Experimental Examples 16 to 18 employing t-C$_4$H$_9$OH or the like as the solvent show a slightly decreased selectivity, but the solvent used is usable. On the other hand, Experimental Examples 19 to 22 employing other highly polar solvents such as C$_2$H$_5$OH have a tendency that selectivities are decreased more. Since the conversion rate and selectivity are thus affected by the reaction solvent, the solvent is preferably selected and used in light of other reaction conditions as well.

On the other hand, it is seen that both the conversion rate and the selectivity are considerably dropped in Experimental Example 23 wherein the reaction was carried out as in Experimental Example 3 except the use of the ligand in which —Cl is replaced by —CH$_3$ in the allyl ester type of the formula (1); that, especially, the conversion rate is quite low in Experimental Example 24 wherein the ligand concentration was changed to 0.1 mM and namely the amount of the catalyst was decreased to 1/10, as compared with that in Experimental Example 5 wherein the amount of the catalyst was similarly decreased to 1/10; and that this ligand in which —Cl is replaced by —CH$_3$ cannot be put into practical use. It can also be understood that the conversion rate are further low in Experimental Example 25 wherein the reaction was carried out as in Experimental Example 3 except the use of a ligand in which —Cl is replaced by a phenyl group, as compared with not only that in Experimental Example 3, but also that in Experimental Example 23, and that this ligand wherein in which —Cl is replaced by a phenyl group cannot either be put into practical use.

Example 4

Production of Various α-Alkenyl Cyclic Ethers Using Various Starting Materials

As indicated in Table 2, an α-alkenyl cyclic ether compound represented by the above formula (14) and α-alkenyl cyclic ethers of Experimental Examples 26 to 37 represented by the following formulae (15) to (25) were produced by using the above compounds (a) to (l). A reaction was carried out under the standard conditions in Example 2 except the following differences, namely, under the conditions that starting material concentration: 100 mM; ligand concentration: 1 mM; solvent: DMA; reaction temperature: 100° C.; and reaction period of time: 1 hour.

There are differences from the standard conditions:
(1) the concentration of the starting material was defined as 1000 mM in Experimental Example 26 employing the compound (a);
(2) the reaction period of time was defined as 3 hours in Experimental Example 32 employing the compound (g);
(3) the reaction temperature was defined as 70° C. and the reaction period of time was defined as 10 hours in Experimental Example 33 employing the compound (h);
(4) a solvent mixture of t-C$_4$H$_9$OH and DMA in a mass ratio of 10:1 was used as the solvent in Experimental Examples 35 to 37 employing the compounds (j) to (l); and
(5) the above requirement (5) was adopted and the reaction period of time was defined as 24 hours in Experimental Example 36.

The enantioselectivity (er) in Experimental Examples 26 to 37 was obtained in the same manner as described above. The isolation yield was obtained by distributing a reaction solution with 3 mL of a solvent mixture of pentane and ether (mass ratio of 3:1) and 5 mL of water, filtering an organic layer with a silica gel, then carefully concentrating the filtrate under the conditions of 0° C. and 50 mmHg, then isolating the product and measuring the weight thereof (except Experimental Examples 27 and 29).

The results are shown in Table 2.

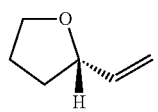

(15)

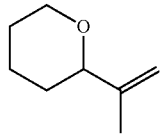

(16)

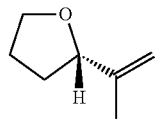

(17)

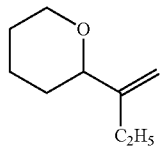

(18)

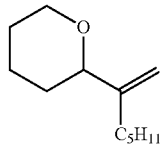

(19)

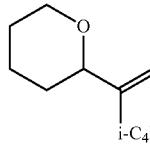

(20)

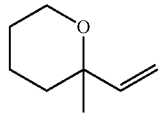

(21)

(22)

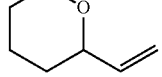

(23)

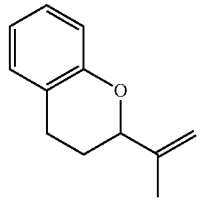

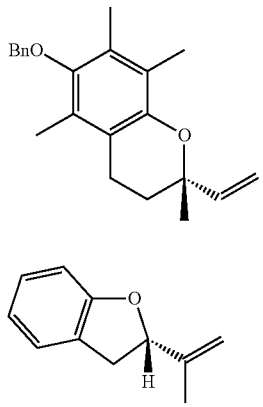

(24)

(25)

In the meantime, Bn represents a benzyl group (C₆H₅CH₂—) in the formula (24).

TABLE 2

| Experimental Example | Starting Material | Cyclic Ether | Isolation Yield [%] | er |
|---|---|---|---|---|
| 26 | Compound (a) | formula (14) | 90 | 97:3 |
| 27 | Compound (b) | formula (15) | — | 94:6 |
| 28 | Compound (c) | formula (16) | 87 | 98:2 |
| 29 | Compound (d) | formula (17) | — | 97:3 |
| 30 | Compound (e) | formula (18) | 93 | 98:2 |
| 31 | Compound (f) | formula (19) | 98 | 98:2 |
| 32 | Compound (g) | formula (20) | 94 | 98:2 |
| 33 | Compound (h) | formula (21) | 92 | 96:4 |
| 34 | Compound (i) | formula (22) | 92 | 96:4 |
| 35 | Compound (j) | formula (23) | 98 | 97:3 |
| 36 | Compound (k) | formula (24) | 97 | 97:3 |
| 37 | Compound (l) | formula (25) | 98 | 99:1 |
| 38 | Compound (m) | formula (26) | — | — |

According to the results shown in Table 2, it is seen that, when the compounds (b) to (l) different, in structure of $R^6$ or the like, from the compound (a) are used as the starting material, various α-alkenyl cyclic ethers of the above formulae (15) to (25) having a 5-membered ring ether structure or a 6-membered ring ether structure are obtained. The isolation yield is sufficiently high in all the Experimental Examples other than Experimental Examples 27 and 29 wherein boiling point of products is low. In addition, all of Experimental Examples 26 to 37 show high "er", and the selectivity of the (S)-substance is quite high, >99%, especially, in Experimental Example 37. The conversion rates were quite high, more than 99%, in all of Experimental Examples 26 to 37, though not indicated in Table 2.

On the other hand, when the compound (m) having one more methylene group possessed by $R^6$ than that of the compound (a) was used, namely, in the case of Experimental Example 38 employing a compound expected to cause the production of cyclic ether of the following formula (26) having a 7-membered ring ether structure, no cyclic ether was produced.

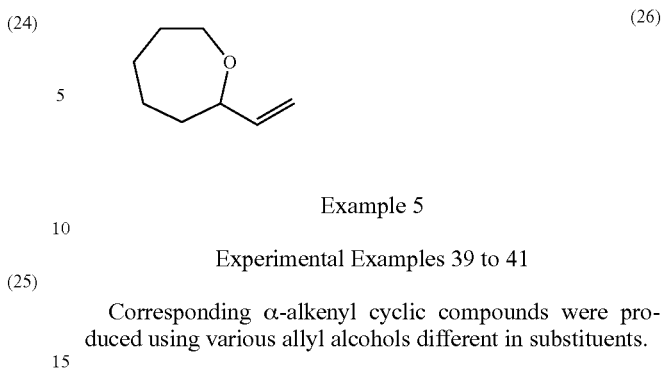

(26)

Example 5

Experimental Examples 39 to 41

Corresponding α-alkenyl cyclic compounds were produced using various allyl alcohols different in substituents.

Experimental Example 39

Cyclodehydration Reaction of Meldrum Acid Type Allyl Alcohol

Into a 20 mL-volume reaction tube with a Young valve, 300 μL of a dichloromethane solution of 2-(E)-5-hydroxypenta-3-ene-1-yl Meldrum acid as a starting material (A solution having a concentration of 333 mM was used and the amount of the starting material was accordingly 100 μmol.) was weighed and put under an argon gas stream. This solution was concentrated under reduced pressure, and 1.00 mL of dichloromethane was added thereto. Then, the solution was subjected to freeze deaeration three times. Next, 0.43 mg (0.001 mmol) of a catalyst precursor represented by the formula (5) and 100 μL of an allyl ester type ligand represented by the formula (1) (A dichloromethane solution having a concentration of 10.0 mM was used and the amount of the ligand was accordingly 1.00 μmol.) were added to a dried 20 mL-volume Schlenk tube with a Young valve which was filled with argon and in which a magnetic stirring rod was put. Then, the solution was carefully concentrated under reduced pressure, and returned to normal pressure with argon. Next, the solution of the starting material prepared in the above manner was added using a canula, and stirred in an oil bath at 100° C. After 1 hour, the Young valve was replaced by a septum stopper under an argon gas stream, and the reaction solution (about 200 μL) was transferred to a sample bottle using a canula. Next, the solution was concentrated with an evaporator, and then the ¹H-NMR spectrum was measured to confirm quantitatively that 8,8-dimethyl-1-vinyl-7,9-dioxaspiro[4,5]decan-6,10-dione had been produced at a conversion rate of 99% or more. The enantiomer ratio was determined by the gas chromatography analysis of the product [column: "CHIRAL-DEX B-PM" (0.25 mm×0.125 μm×30 m); temperature: 100° C.; sprit ratio: 100:1]. As a result, the ratio between the integrated values at the respective peaks was 83:17.

Experimental Example 40

Cyclodehydration Reaction of Sulfonylamino Allyl Alcohol

Into a 20 mL-volume reaction tube with a Young valve, 300 μL of a dichloromethane solution of (E)-6-p-toluenesulfonylaminohexan-2-ene-1-ol as a starting material (A solution having a concentration of 333 mM was used and the amount of the starting material was accordingly 100 μmol.) was weighed and put under an argon gas stream. This solution was concentrated under reduced pressure, and 1.00 mL of DMA was added thereto. Then, the solution was subjected to freeze deaeration three times. Next, 0.43 mg (0.001 mmol) of a catalyst precursor represented by the formula (5) and 100 μL of the allyl ester type ligand of the formula (1) produced in Example 1 (A dichloromethane solution having a concentration of 10.0 mM was used and the amount of the ligand was accordingly 1.00 μmol.) were added to a dried 20 mL-volume Schlenk tube with a Young valve which was filled with argon and in which a magnetic stirring rod was put. Then, the solution was carefully concentrated under reduced pressure, and returned to normal pressure with argon. Next, the solution of the starting material prepared in the above manner was added using a canula, and stirred in an oil bath at 100° C. After 1 hour, the Young valve was replaced by a septum stopper under an argon gas stream, and the reaction solution (about 200 μL) was transferred to a sample bottle using a canula. Next, the solution was concentrated with an evaporator, and then the $^1$H-NMR spectrum was measured to confirm quantitatively that N-p-toluenesulfonyl-2-ethenylpyrrolidine had been produced at a conversion rate of 99% or more. The enantiomer ratio was determined by the high-performance liquid chromatography analysis of the product [column: "CHIRALCEL AD-H" (0.25 mm×0.125 μm×30 m); solvent: solvent mixture of hexane and 2-propanol in a mass ratio of 95:5; flow rate: 0.5 mL/min.]. As a result, the ratio between the integrated values at the respective peaks was 96:4.

Experimental Example 41

Cyclodehydration Reaction of Carboxyallyl Alcohol

Into a 20 mL-volume reaction tube with a Young valve, 144 mg (1.00 mmol) of (E)-6-hydroxy-4-hexenoic acid as a starting material was weighed and put under an argon gas stream. After the addition of 10 mL of DMA to this, the solution was subjected to freeze deaeration three times. Next, 4.34 mg (10.0 μmol) of a catalyst precursor represented by the formula (5) and 100 μL of the allyl ester type ligand of the formula (1) produced in Example 1 (A dichloromethane solution having a concentration of 10.0 mM was used and the amount of the ligand was accordingly 10.0 μmol.) were added to a dried 50 mL-volume Schlenk tube with a Young valve which was filled with argon and in which a magnetic stirring rod was put. Then, the solution was carefully concentrated under reduced pressure, and returned to normal pressure with argon. Next, the solution of the starting material prepared in the above manner was added using a canula, and stirred in an oil bath at 100° C. After 20 minutes, the reaction mixture was subjected to silica gel column chromatography (sample: 30 g; developing solvent: ether) to isolate 4-ethenylbutyrolactone. Then, Kugelrohr distillation (35° C.; 0.01 mmHg) was carried out to obtain a colorless oily product (75.6 mg; conversion rate: 70%). The enantiomer ratio was determined by the gas chromatography analysis of the product [column: CHIRALDEX B-PM (0.25 mm×0.125 μm×30 m); temperature: held at 40° C. for 5 minutes (temperature increasing speed: 1° C./min.) and held at 65° C. for 65 minutes; sprit ratio: 100:1]. The ratio between the integrated values at the respective peaks was 99:1.

The present invention is not limited by the above description regarding embodiments, and embodiments variously modified depending on the purpose, intended use and the like can be carried out within the scope thereof. For example, in the above Examples, the ligand and the catalyst precursor were mixed, and then the starting material was incorporated into the mixture to cause a reaction. However, it is also possible to produce an α-alkenyl cyclic compound by dissolving the ligand, catalyst precursor and starting material in an appropriate reaction solvent at the same time. Further, a solution in which the ligand and the catalyst precursor are dissolved can be incorporated into a solution in which the starting material is dissolved, thereby causing a reaction.

The invention claimed is:

1. A ligand having a formula selected from the group consisting of formulae (1) to (4):

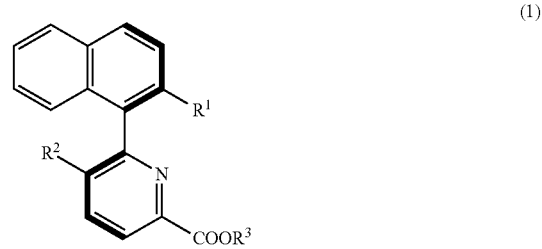

(1)

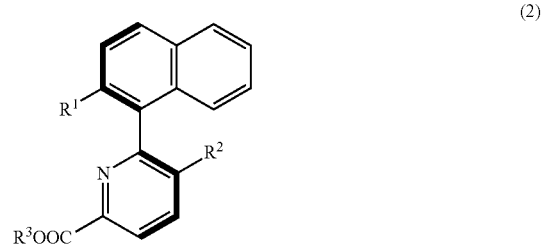

(2)

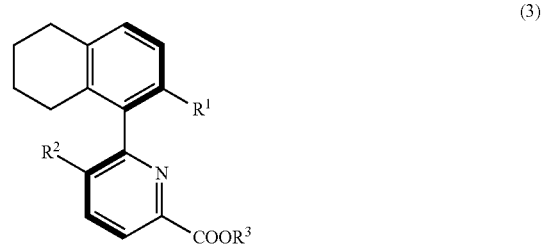

(3)

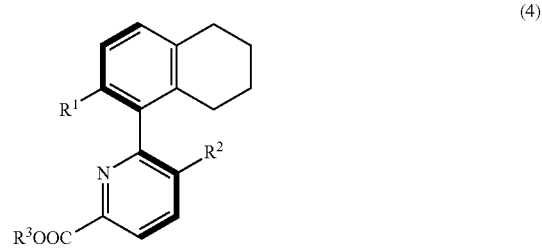

(4)

wherein:
$R^1$ is —Cl or —Br;
$R^2$ is —CH$_3$ or —CF$_3$; and
$R^3$ is —CH$_2$—CH═CH$_2$ or —H.

2. The ligand of claim 1, having formula (1), wherein $R^1$ is —Cl and $R^2$ is —CH$_3$.

3. The ligand of claim 1, having formula (2), wherein $R^1$ is —Cl and $R^2$ is —CH$_3$.

* * * * *